US00PP12623P2

(12) United States Plant Patent

Olesen et al.

(10) Patent No.: US PP12,623 P2
(45) Date of Patent: May 14, 2002

(54) SHRUB ROSE PLANT NAMED 'POULTERP'

(76) Inventors: L. Pernille Olesen; Mogens N. Olesen, both of Hillerødvejen 49, DK-3480 Fredensborg (DK)

( * ) Notice: Subject to any disclaimer, the term of this patent is extended or adjusted under 35 U.S.C. 154(b) by 0 days.

(21) Appl. No.: 09/273,165

(22) Filed: Mar. 19, 1999

(51) Int. Cl.[7] ..... A01H 5/00
(52) U.S. Cl. ..... Plt./103
(58) Field of Search ..... Plt./103, 117, 124

(56) References Cited

PUBLICATIONS

UPOV–ROM, 2000/04, Plant Variety Database, GTI Jouve Retrieval Software, 2 citations for 'POULterp'.*
Copy of EU 3389, granted Jul. 6, 1998 and Application No. EU 1810/95 filed Aug. 23 1995.*
Copy of PL 000853, granted Feb. 22, 1999 and application No. PL 038, filed Jan. 27,1997.*

* cited by examiner

*Primary Examiner*—Howard J. Locker

(57) ABSTRACT

A new shrub rose plant which has abundant, white flowers which are present on the plant continually throughout the growing season. Its low spreading habit and very glossy, disease resistant foliage demand limited maintenance, making it ideal for use in landscapes. The variety is suitable for propagation on its own roots, as well as, a traditionally budded plant. This new and distinct variety has shown to be uniform and stable in the resulting generations from asexual propagation.

1 Drawing Sheet

SUMMARY OF THE INVENTION

The present invention constitutes a new and distinct variety of shrub rose plant which originated from a controlled crossing during the summer of 1987 between 'Fairyland' (non-patented) and 'POULcat' (non-patented). The two parents were crossed and the resulting seeds were planted in a controlled environment. The new variety is named 'POULterp'.

The new rose may be distinguished from its seed parent, 'Fairyland', by the following combination of characteristics:

1. The seed parent has pink double flowers in trusses while 'POULterp' has smaller white flowers in sprays;

2. The seed parent's blooms typically have 24 petals, while 'POULterp's blooms average 38 petals.

The new variety may be distinguished from its pollen parent,'POULcat' created by the same inventors, by the following combinations of characteristics:

1. The pollen parent is a groundcover variety that spreads vigorously, while 'POULterp' has less vigorous growth with slightly arching canes;

2. The pollen parent blooms once or twice in a growing season; whereas, 'POULterp' blooms continuously throughout the season.

The objective of the hybridization of this rose variety for garden and landscape use was to create a new and distinct variety with unique qualities, such as:

1. Abundant, white flowers which are present on the plant continually throughout the growing season;

2. A low spreading habit and very glossy, disease resistant foliage that demands limited maintenance, making it ideal for use in landscapes;

3. Suitable for production on its own roots and as a traditionally budded plant.

This combination of qualities is not present in previously available commercial cultivars of this type and distinguishes 'POULterp' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULterp' was selected by the inventors in March, 1987 as a single plant from the progeny of the aforementioned hybridization.

Asexual reproduction of 'POULterp' by cuttings and traditional budding was first done by L. Pernille and Mogens N. Olesen in July, 1987, in their nursery in Fredensborg, Denmark. This initial and other subsequent propagations conducted in controlled environments have demonstrated that the characteristics of 'POULterp' are true to type and are transmitted from one generation to the next.

BRIEF DESCRIPTION OF THE DRAWING

The accompanying color illustration shows, as true as is reasonably possible to obtain in color photographs of this type, the typical characteristics of the buds, flowers, leaves, and stems of 'POULterp'. Specifically illustrated in SHEET 1:

1. Stem showing branching and the attachment of leaves, buds, and peduncles;

2. Flower bud, partially opened bud, and open blooms;

3. Flower petals, detached;

4. Sepals and pedicel;

5. Flowering stem as well as a bare stem exhibiting thorns;

6. Leaves.

DETAILED DESCRIPTION OF THE VARIETY

The following is a description of 'POULterp', as observed in its growth during August, 1998 in a field nursery in Jackson County, Oreg. Color references are made using The Royal Horticultural Society (London, England) Colour Chart, 1995, except where common terms of color are used.

For a comparison, the nearest existing rose variety is 'POULcov', a variety by the same inventors described and illustrated in U.S. Plant Pat. No. 10,648, granted Oct. 20, 1998. Chart 1 details several physical characteristics of the applicant and the comparison variety.

CHART 1

| | 'POULterp' | 'POULcov' |
|---|---|---|
| Flower Color. | White Group 155D. | White Group 155D. |
| Flower type. | Double. | Semi-double. |
| Foliage size. | Smaller. Average 30 mm (w) × 70 mm (l). | 30–50 mm (w) 80–100 mm (l). |
| Plant habit. | Lateral growing, more spreading ground cover habit. | Compact, lateral branching with an upright habit. |
| Foliage. | Glossy. | Slightly glossy. |

Parents:
- *Seed parent.*—'Fairyland'.
- *Pollen parent.*—'POULcat'.

Classification:
- *Botanical.*—*Rosa hybrida.*
- *Commercial.*—Shrub.

FLOWER AND FLOWER BUD

Blooming habit: Continuous.

Flower bud:
- *Size.*—Upon opening, 15 mm average length from base of receptacle to end of bud.
- *Bud form.*—Short and ovoid.
- *Bud color.*—As sepals unfold and at ¼ opening, White Group 155D.
- *Sepals.*—Yellow-Green Group 144B. Weak foliaceous appendages on all five sepals. Surfaces of sepals slightly pubescent. Stipitate glands are present in moderate numbers on the outer side and along the edges of the sepals. Sepals have intonations of Red Group 46A.
- *Receptacle.*—Surface: Smooth. Shape: Pear. Size: Medium. 8 mm (h)×4 mm (w). Color: Yellow-Green Group 144A. Some receptacles with strong intonations of Greyed-Purple Group 186B.
- *Peduncle.*—Surface: Smooth. Length: 15–20 mm average length. Color: Yellow-Green Group 144C with intonations of Greyed-Purple 178B in areas exposed to direct sunlight. Strength: Erect.
- *Borne.*—Typically with 4–10 buds per flowering stem. A flowering stem may have up to 4–8 lateral flowering shoots which develop during the flowering of apical tip.

Flower bloom:
- *Size.*—Small. Average flower diameter is 35 mm when opened.
- *Form.*—Shape of flower when viewed from the side: Upon opening, upper part: Flat. Upon opening, lower part: Convex. Open flower, upper part: Flattened convex. Open flower, lower part: Concave.
- *Petalage.*—Double. Average range: 35–40 petals under normal conditions with 2 to 5 petaloids.

Color:
- *Upon opening.*—Petals: Upper Surface: White Group 155B. Reverse Side: White Group 155C. Basal petal spots: Outer Side: Green-White Group 157B. Inner Side: Green-White Group 157B.
- *After opening.*—Outermost petals: Upper Surface: White Group 155D. Reverse Side: White Group 155B. Innermost petals: Upper Surface: White Group 155B–C. Reverse Side: White Group 155B–C. Basal petal spots: Outer Side: Green-White Group 157B. Inner Side: Green-White Group 157B.

General tonality: On open flower, White Group 155C. No change in the general tonality at the end of the third day. Afterwards, general tonality is Yellow-White Group 158C.

Petals:
- *Petal reflex.*—Slight.
- *Petal edge.*—Uniform.
- *Petaloids.*—Present. Quantity: 2–5.
- *Fragrance.*—Moderate wild rose scent.
- *Duration.*—As a cut flower 1 to 2 days. Duration of individual blooms 2–3 days.
- *Thickness.*—Average.
- *Shape.*—Round.
- *Form.*—Reflexed slightly.
- *Arrangement.*—Informal.

Reproductive organs:
- *Pollen.*—Color: Green-White Group 157B. Quantity: Limited abundance.
- *Anthers.*—Size: Medium. Color: Yellow-Green Group 1D. Quantity: Limited to average.
- *Filaments.*—Color: Yellow-Green Group 145B.
- *Stigmas.*—Slightly superior in location to anthers. Color: Yellow-Green Group 145D with some intonations of Greyed-Purple Group 186C.
- *Styles.*—Color: Yellow-Green Group 145D.
- *Hips.*—None observed.

PLANT

Plant growth: Vigorous shrub with arching canes. Height of 45–60 cm and width of 120 cm to 150 cm. The canes are numerous and long, arching to create a dense cover.

Stems:
- *Length.*—45–60 cm.
- *Color.*—Young wood: Yellow-Green 145A. Greyed-Red Group 178A on the areas of stems exposed to sunlight. Older wood: Yellow-Green Group 145A.
- *Thorns.*—Incidence: 3 to 5 thorns per 10 cm of stem. Size: Average length: 5 mm. Color: Immature: Yellow-Green Group 145C with intonations of Greyed-Purple Group 183D. Mature: Greyed-Purple Group 183B. Shape: Concave.
- *Surface.*—Young wood: Smooth. Older Wood: Smooth.

Plant foliage: Normal number of leaflets on leaves in middle of the stem: 7 leaflets.
- *Leaf size.*—Small. 70 mm (l)×30 mm (w).
- *Abundance.*—Very abundant.
- *Color.*—Upper Leaf Surface: Green Group 137A. Lower Leaf Surface: Green Group 137C. Juvenile foliage: Upper surface: Green Group 143B. Lower surface: Green Group 143B. Anthocyanin: Present on juvenile foliage, specifically at leaflet margins, rachis, stipules, and petiole.

Plant leaves and leaflets:

*Stipules.*—Present. Stipitate glands present along margins. Size: 10 mm (l)×5 mm (w). Color: Yellow-Green Group 144B.

*Petiole.*—Length: 15 mm. Color: Yellow-Green Group 145B. Margins: Stipitate glands along margins of the stipules. Prickles: Limited.

*Rachis.*—Color: Green Group 137D. On juvenile leaflets, the upper surface has intonations of Greyed-Purple Group 185C. Lower surfaces are Yellow-Green Group 145C. Margins: With stipitate glands. Prickles: Moderate number.

*Leaflet.*—Number: Range 5–9. Most commonly 7. Edge: Serrated. Shape: Elliptic with a cuspidate tip.

*Texture.*—Glossy. Thin texture.

Disease resistance: Exceptional resistance to mildew, black spot, and Botrytis under normal growing conditions in Jackson County, Oreg.

Winter hardiness: POULterp has been found to be winter hardy in Fredensborg, Denmark and in Jackson County, Oreg.

We claim:

1. A new and distinct variety of rose plant of the shrub class, substantially as herein illustrated and described as a distinct and novel rose variety due to its abundant, pure white flowers, low spreading habit, glossy and disease resistant foliage, good growth on its own roots as well as a traditionally budded plant and low maintenance requirements which make the variety ideal for use in nurseries and landscapes.

* * * * *

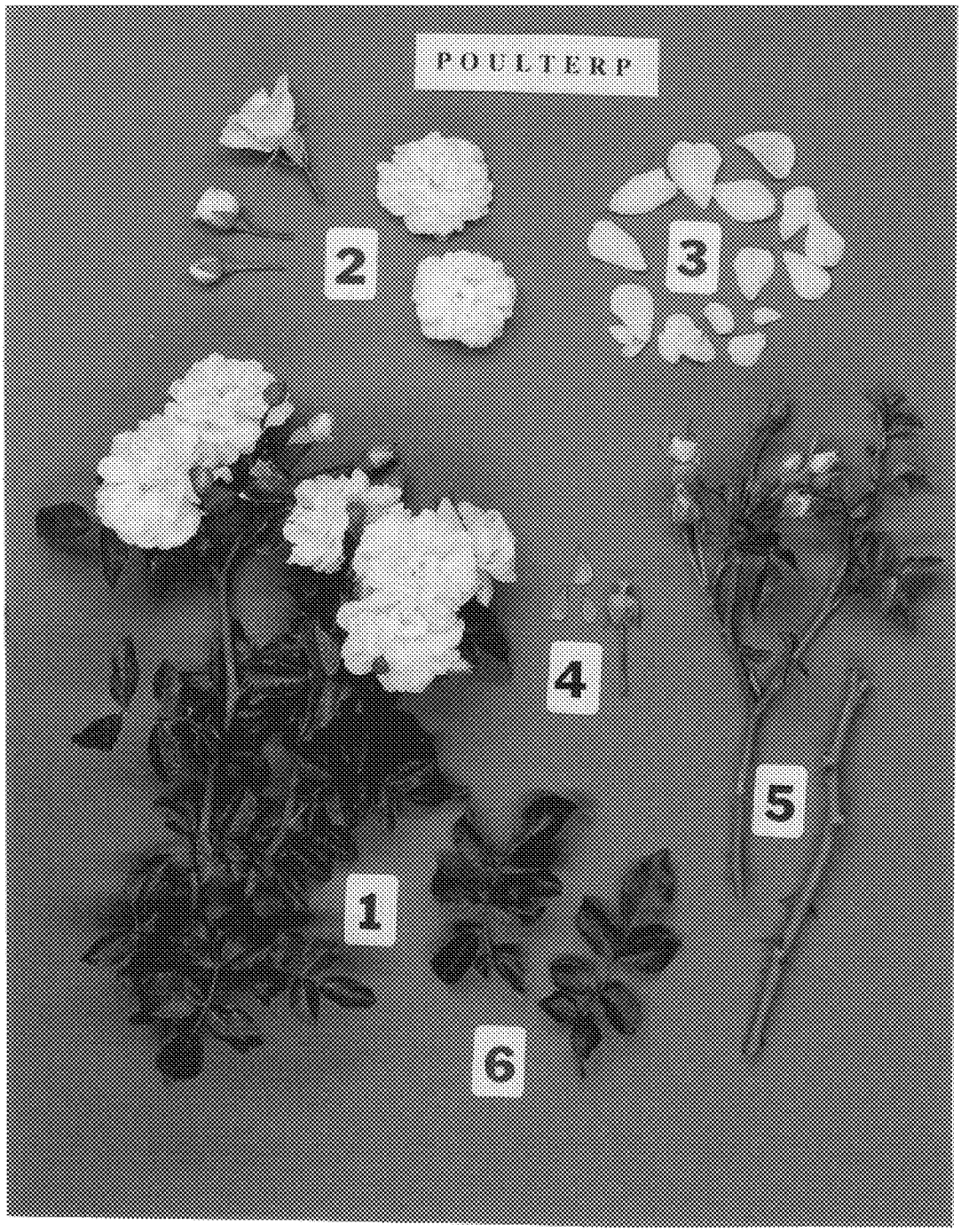
POULTERP
2
3
4
5
1
6